United States Patent [19]

Burke

[11] Patent Number: 5,545,168
[45] Date of Patent: Aug. 13, 1996

[54] APPARATUS FOR BOTH TENSIONING AND CRIMPING A SURGICAL WIRE

[76] Inventor: Dennis W. Burke, 245 Highland Ave., Milton, Mass. 02186

[21] Appl. No.: 212,038

[22] Filed: Mar. 11, 1994

[51] Int. Cl.$^6$ .................................................. A61B 17/82
[52] U.S. Cl. ........................ 606/74; 606/103; 606/144; 606/148; 140/106
[58] Field of Search ............................ 606/103, 74, 61, 606/60, 72, 86, 135, 144, 148; 140/93.2, 93.4, 105, 106; 7/125, 126, 127, 128, 900

[56] References Cited

U.S. PATENT DOCUMENTS

| | | |
|---|---|---|
| 1,641,077 | 8/1927 | Fouquet . |
| 2,049,361 | 7/1936 | Ericsson . |
| 2,455,609 | 12/1948 | Scheib . |
| 3,507,270 | 4/1970 | Ferrier .................................. 128/668 |
| 4,050,464 | 9/1977 | Hall . |
| 4,128,100 | 12/1978 | Wendorff . |
| 4,587,963 | 5/1986 | Leibinger et al. . |
| 4,966,600 | 10/1990 | Songer et al. . |
| 5,057,113 | 10/1991 | Mingozzi . |
| 5,116,340 | 5/1992 | Songer et al. . |
| 5,122,130 | 6/1992 | Keller ........................................ 606/61 |
| 5,236,434 | 8/1993 | Callicrate ................................ 606/135 |

FOREIGN PATENT DOCUMENTS

| | | | |
|---|---|---|---|
| 532698 | 9/1931 | Germany ................................ 606/103 |

*Primary Examiner*—Guy Tucker
*Attorney, Agent, or Firm*—Pandiscio & Pandiscio

[57] ABSTRACT

An apparatus and method for tightening and crimping a surgical wire used for orthopedic purposes. The apparatus of this invention includes a pair of operating handles which are biased apart and which operate a pair of opposed jaws to which they are connected. Disposed on opposite sides of the operating handles are a pair of capstans. The jaws are adapted to hold a crimp member therein without deforming it while opposite ends of a length of wire are passed through the crimping member in opposite directions. Each end of the wire is wrapped about an associated capstan. A ratchet handle simultaneously rotates both capstans to wrap the opposite ends of the wire. Once the desired traction force has been achieved, the jaws are further activated to crimp the crimp member. A ring-shaped crimp member is also disclosed which has a central opening extending along the axis thereof and two parallel channels, one channel being disposed on either side of the central opening.

6 Claims, 7 Drawing Sheets

5,545,168

APPARATUS FOR BOTH TENSIONING AND CRIMPING A SURGICAL WIRE

FIELD OF THE INVENTION

This invention relates generally to orthopedic instruments, more particularly to an instrument which both tensions and crimps a surgical wire used for the positioning and fixation of bone parts or sections during osteosynthesis.

BACKGROUND OF THE INVENTION

Surgical wires are used in a variety of surgical procedures, such as, for example reconstructive spine surgeries (such as fusions), spine trauma surgery, total hip arthroplasty, open heart surgery, closures of the sternum, oral/facial surgery to fix mandibular fractures and the like, repair of trochanteric osteotomies and fracture fixation including long bone fractures, adjunct fixation of plates to bone, repair of olecronon fractures, repair of patella fractures and the repair, reconstruction or augmentation of soft tissues such as sprained or ruptured ligaments and tendons.

In surgical and orthopedic operative techniques, it is frequently necessary to fix bone parts, which have been separated surgically or because of fracture, in an exact mutual position and to join them together under pressure. For such osteosynthesis, a monofilament wire is used to encircle broken bones to hold them together. Multi-filament cables also are known for such uses. These wires or cables must either be crimped or twisted together to secure them with a desired tension and a desired location.

The amount of force which is applied to the bone is very important. If too great a tractive force is applied by the cable or wire, a vascular necrosis could be created in the bone around which the cable or wire is wrapped. However, if the tractive force is too low in magnitude, the bone parts are not properly held in the desired position for proper mechanical fixation thereof. Also, if a wire is used and it is twisted too tightly, a fracture of the wire could occur. Thus, a great deal of skill is required to provide the proper tractive force or tension on the wire or cable at the time of installation, even if the surgeon uses the many tools which are commercially available.

Often, the wire or cable must be used in a subcutaneous area. Therefore, it is desirable to render the bulk of the wire or cable as well as the joint where the wire or cable is affixed to itself as compact as possible to minimize discomfort to the patient and damage to the surrounding tissue.

Crimping is typically preferred to twisting of a wire or cable. Twisting of a wire tends to produce a bulky joint, and can cause the wire to break, requiring replacement of the wire. Also, twisting of the wire leaves exposed sharp ends which can cause irritation and damage to the surrounding tissue. Moreover, experimental data demonstrates that crimped wire is stronger than wire that has been twisted or tied. Finally, if the ends of a wire are twisted together, the resulting tractive force of the wire can only be determined by feel and therefore, often, force is very inaccurately applied to the bone.

Even crimping has its drawbacks, primarily because existing tools are not convenient to use. More than one tool often is required to tighten and then crimp a wire. A first tool must tighten the wire to its desired tractive force, and a second tool is required to crimp the wire to hold it in position. As a result, with such systems, a single person has difficulty in doing all that needs to be done with the required degree of accuracy and care.

None of the available prior art systems adequately solves all of the foregoing problems. In particular, a system manufactured by Codman & Shurtleff, Inc. requires the use of a torque driver for tightening the cable, and a separate set of pliers for cinching the cable. Another system developed by John M. Cuckler at the University of Pennsylvania requires a self-locking tensioner which maintains the desired tension, and a second crimper for securing the wire in place. The Dall-Miles trochanter cable grip system offered by Howmedica requires separate cable tensioning and crimping devices. All of these systems necessitate considerable dexterity on the part of the surgeon, and can be difficult to use in circumstances in which the surgical site is difficult to reach or in which the bone has been fractured in a number of places.

Apparatus has been designed to both tension and crimp the wire. However, such devices have not achieved broad commercial success, because they are often difficult to use. In particular, in U.S. Pat. No. 5,116,340, operation of the tightening device requires a torque wrench which requires two hands and can be awkward to use. The apparatus shown in U.S. Pat. No. 4,587,963, provides a separate arm for tightening which is spaced from the handles of the instrument. The position of this arm renders the apparatus difficult to use with one hand.

It is therefore an object of the present invention to provide a single tool which both tightens and crimps a surgical wire.

It is another object of the present invention to provide a tool which both tightens and crimps a surgical wire and which can be readily used by the surgeon, with one hand.

It is another further object of the present invention to provide a tool and method which produces a high strength, low bulk crimp suitable for a subcutaneous location.

SUMMARY OF THE INVENTION

The above and other objects are achieved in accordance with the present invention in which, in one aspect of the invention, a single apparatus is provided which both tightens with the desired tension and crimps a surgical wire. The apparatus is manually operated and can be held and used to both crimp and tighten with one hand. The apparatus includes a pair of operating handles which are connected through links to an opposed pair of crimping jaws. The jaws are configured to have a recess at their operating ends which holds a crimp member. Guides are provided on the jaws for accommodating ends of a surgical wire which pass through the crimp and extend downwardly toward the pivot of the operating handles. As the jaws are opened by operation of the handles to receive a crimp member, a movable stop allows retention of the jaws with a spacing which holds the crimp member in position, but does not deform it. Subsequent actuation of the operating handles produces crimping of the crimp member. Two capstans are provided, one on either side of the operating handles. The capstans are aligned with the pivot of the operating handles, each capstan being adapted to receive an end of the surgical wire. Both capstans are related simultaneously by movement of a ratchet handle disposed between and substantially in the plane of the operating handles.

In another aspect of the invention a crimp member dispenser having two prongs is provided to facilitate placement of the crimp member in the recess disposed in the ends of the jaws. A preferred crimp member has a substantially donut shape i.e. a ring with a central, axially aligned hole or opening. The crimp member includes two parallel channels passing through the ring in a direction substantially perpendicular to the axis of the ring. These two channels may or may not intersect the centrally disposed hole along edges thereof, and are spaced an amount equal to the spacing between the two prongs of the dispenser. The crimp member is loaded onto the dispenser by inserting the two prongs through the parallel channels in the ring.

In yet another aspect of the present invention, a method is provided for both tightening and crimping of a surgical wire utilizing a single manually operated apparatus which can be held and actuated with a single hand. A crimp member is first loaded into a specifically adapted recess in the distal end of the jaws of the apparatus while still mounted onto the prongs of the dispenser. The channels in the crimp member are aligned in a direction substantially parallel to the pivot axis of the operating handles. The operating handles are grasped and squeezed together to push the jaws together sufficiently to grasp the crimp member. A stop slides between the surfaces of the jaws to prevent the jaws from reopening once pivoting pressure is removed from the operating handles. When the desired holding force has been applied to the crimp member, the stop is located between the jaws to hold them in that position to retain the crimp member tightly within the jaws without deforming it. The two prongs of the dispenser are then retracted from the channels in the crimp member.

Thereafter, the surgical wire is wrapped about the bone or bone fragments in a manner well known to those skilled in the art. Each end of the surgical wire is then inserted through one of the channels of the crimp member. One end of the wire passes through one channel in one direction while the other end of the surgical wire passes through the other channel of the crimp member in an opposite direction. Each end of the wire is pulled toward the pivot axis of the handles over an associated guide, and thereafter each end is wrapped about an associated capstan. The capstans preferably are on opposite ends of the pivot axis of the handles. The ratchet handle is actuated, causing the wire to be tensioned by wrapping each end about an associated capstan.

When the desired tension has been achieved, actuation of the ratchet handle ceases. At this point, the operating handles are squeezed together using the same hand which actuated the ratchet handle. Pivoting of the operating handles drives the jaws tightly together and deforms the crimp member to secure the surgical wire in the desired position. Once the crimp member has been sufficiently deformed, the spring loaded stop is released allowing the handles to be released, and permitting the jaws to open. The surgical wire and crimp member are then removed from the jaws, and the free ends of the surgical wire are clipped.

The method and apparatus of this invention provide a quick and easy technique for tightening and crimping a surgical wire using only one hand. The resulting crimp has a high level of strength and low bulk and does not aggravate adjacent tissue surfaces, permitting the use of the method and apparatus of this invention in subcutaneous locations.

BRIEF DESCRIPTION OF THE DRAWINGS

The objects, advantages and features of this invention will be more clearly appreciated from the following detailed description when taken in conjunction with the accompanying drawings in which.

DETAILED DESCRIPTION OF THE PREFERRED EMBODIMENTS

Figure 1:
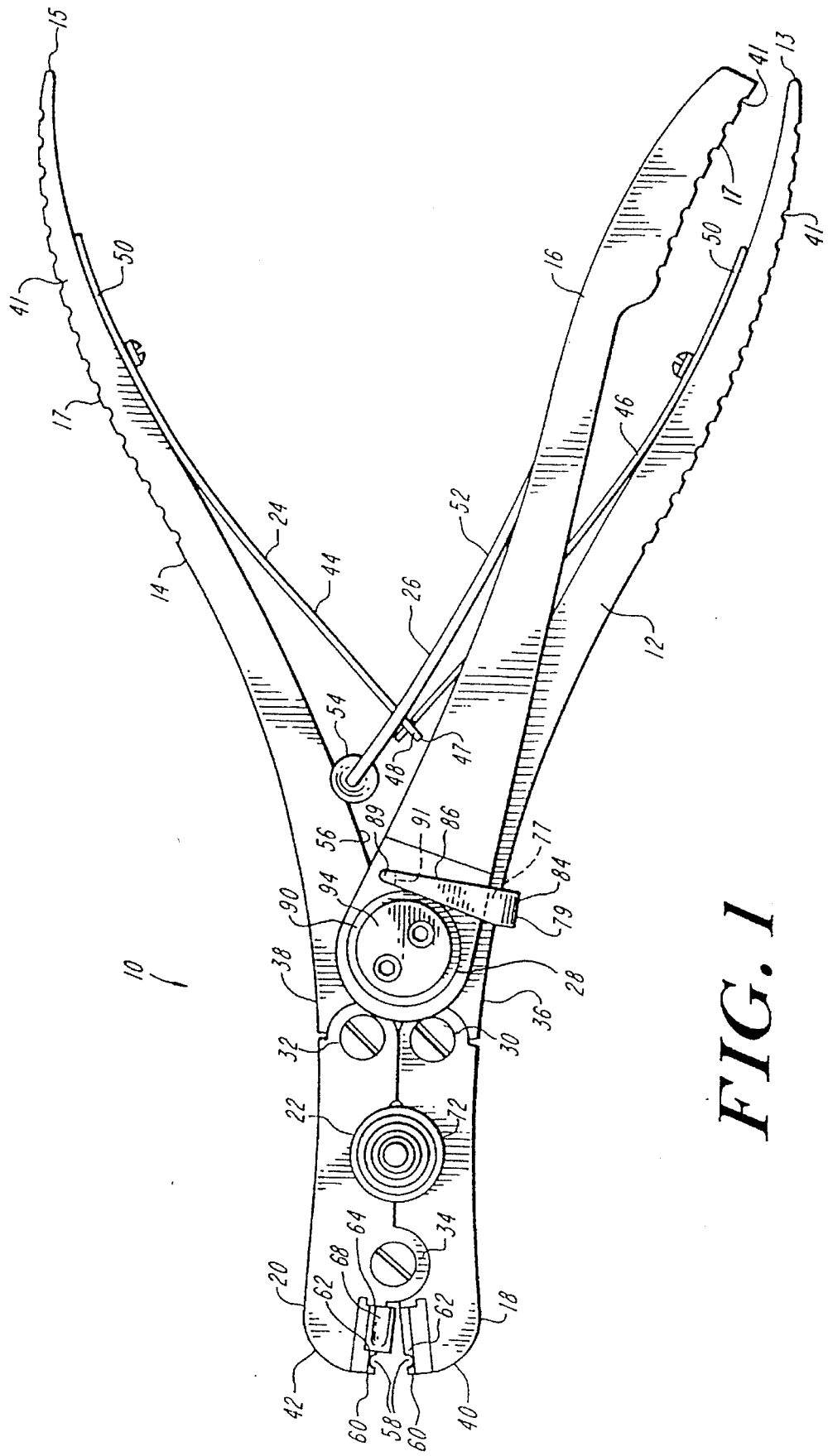
FIG. 1 is an elevation view of one side of the apparatus of this invention.
Figure 2:
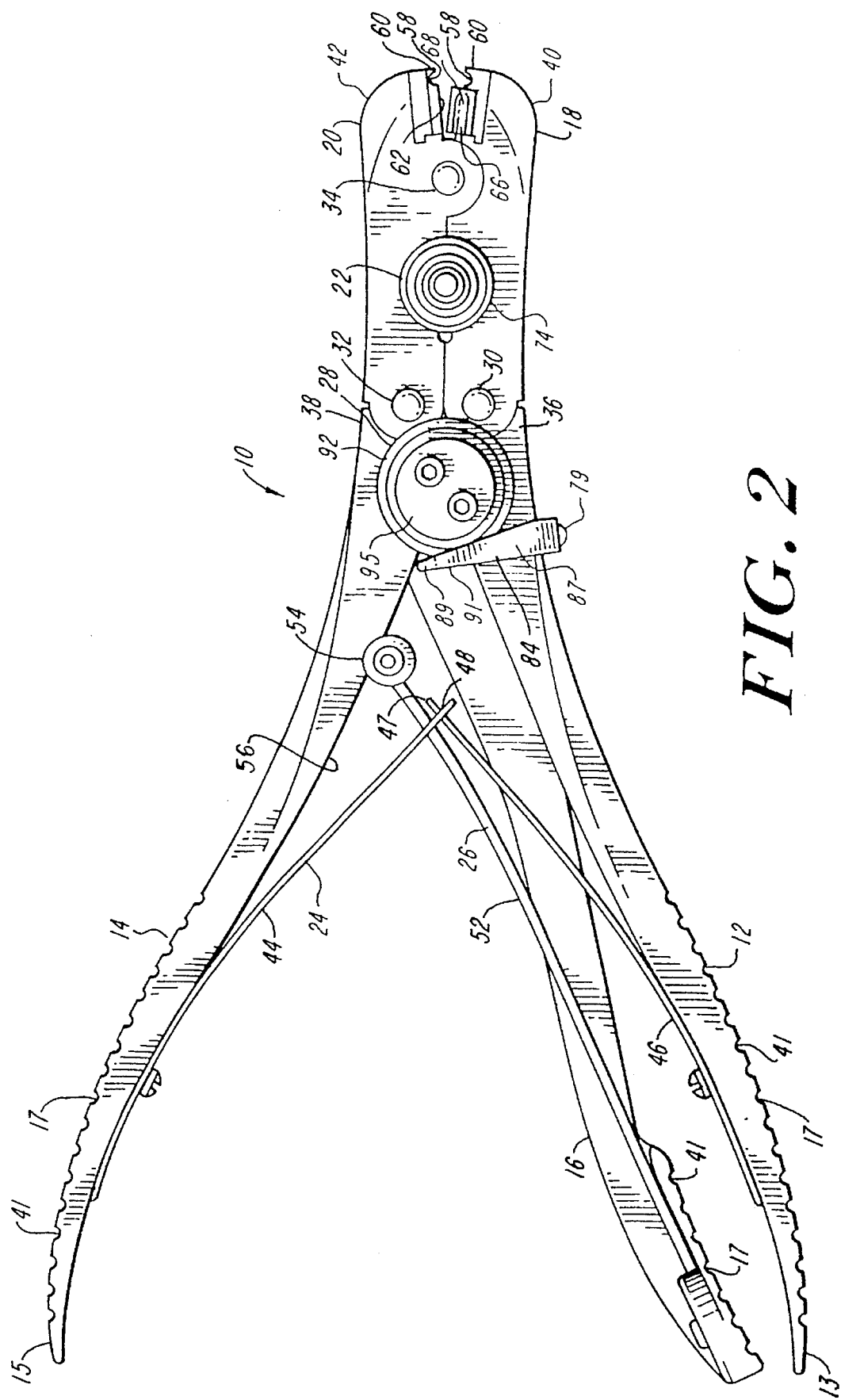
FIG. 2 is an elevation view of the other side of the apparatus of this invention.

With reference now to the drawings, and more particularly to FIGS. 1 and 2 thereof, a preferred embodiment of the apparatus of this invention will now be described. Tightening and crimping apparatus 10 includes a pair of operating handles 12 and 14, a ratchet handle 16, jaws 18 and 20, stop 22, wire holder 84, springs 24 and 26, and pivots 28, 30, 32 and 34.

Handles 12 and 14 are pivotally coupled to one another at pivot 28. Handles 12 and 14 are pivotally secured at respective ends 36 and 38 to respective jaws 18 and 20 at pivots 30 and 32 respectively. Ends 36 and 38 are closely spaced from pivot 28 and are disposed on a side of pivot 28 opposite of proximal ends 13 and 15 of respective handles 12 and 14 to provide the desired mechanical advantage to jaws 18 and 20. Jaws 18 and 20 are pivotally attached to one another at pivot 34, which is positioned closely adjacent the nose ends 40 and 42 of respective jaws 18 and 20 so that the required crimping force is applied to ends 40 and 42. Handles 12 and 14 operate in a conventional manner such that movement of respective proximal ends 13 and 15 towards one another causes handles 12 and 14 to pivot about pivot 28. This movement causes ends 36 and 38 to move apart which pivots jaws 18 and 20 with respect to one another about pivot 34 so that ends 40 and 42 are urged toward one another. Conversely, as the distal ends 13 and 15 of respective handles 12 and 14 move apart, ends 40 and 42 pivot away from one another about pivot 34.

Spring 24 biases proximal ends 13 and 15 of respective handles 12 and 14 away from one another. Spring 26 biases ratchet handle 16 into its home position adjacent handle 12 so that when the ratcheting mechanism is used, as will be described hereinafter, handle 16 is automatically returned to its home position. Spring 24 can be any commonly used mechanism for urging handles 12 and 14 apart at their proximal ends. In one embodiment, spring 24 includes two preformed, resilient, metal strips 44 and 46 which are secured at one end 50 to respective handles 12 and 14 adjacent respective proximal ends 13 and 15 thereof. The opposite ends of strips 44 and 46 are either secured together at point 48, or are configured with interlocking tongues 47 and grooves such that they are urged into constant contact at point 48.

Spring 26 also may be any commonly used biasing mechanism. In one embodiment, spring 26 includes a preformed, resilient metal strip 52 and cam follower 54. One end of strip 52 is attached to the distal end of handle 16. Follower 54 is journalled in the other end of strip 52. Follower 54 rides along cam surface 56 formed on the inside surface of handle 14 during movement of handle 16 about pivot 28. Strip 52 urges handle 16 back to its home position adjacent handle 12 upon the release of a pivoting force on ratchet handle 16.

In a preferred embodiment, each of handles 12 and 14, as well as ratchet handle 16, includes a textured surface 17 to assist in the manual grasping and manipulation thereof. Textured surface 17 may comprise a plurality of parallel slots or depressions 41, abrasions providing a toughened surface or any other type of textured surface which provides the desired tactile sensation and frictional grip.

Ends 40 and 42 each include a recess 58. Recess 58 on each end 40 and 42 is located between an overhanging lip 60 and a lower surface 62. The two recesses 58 on ends 40 and 42 confront each other and together form one large recess sized to accept a crimp member 200, as described hereinafter (See FIG. 3). The space between surface 62 and lip 60 in each recess 58 is approximately equal to the thickness of a crimp member 200 so that crimp member 200 is held in position in combined recesses 58 by overhanging lips 60. Disposed on ends 40 and 42 are respective slotted guides 64 and 66. Guide 64 is disposed on one side of apparatus 10 on end 42 directly behind recess 58, while guide 66 is disposed on the opposite side of apparatus 10 on end 40 behind recess 58. Guides 64 and 66 each include a slot 68 adapted to receive a length of wire 202, as will be more fully described hereinafter.

Figure 6A:
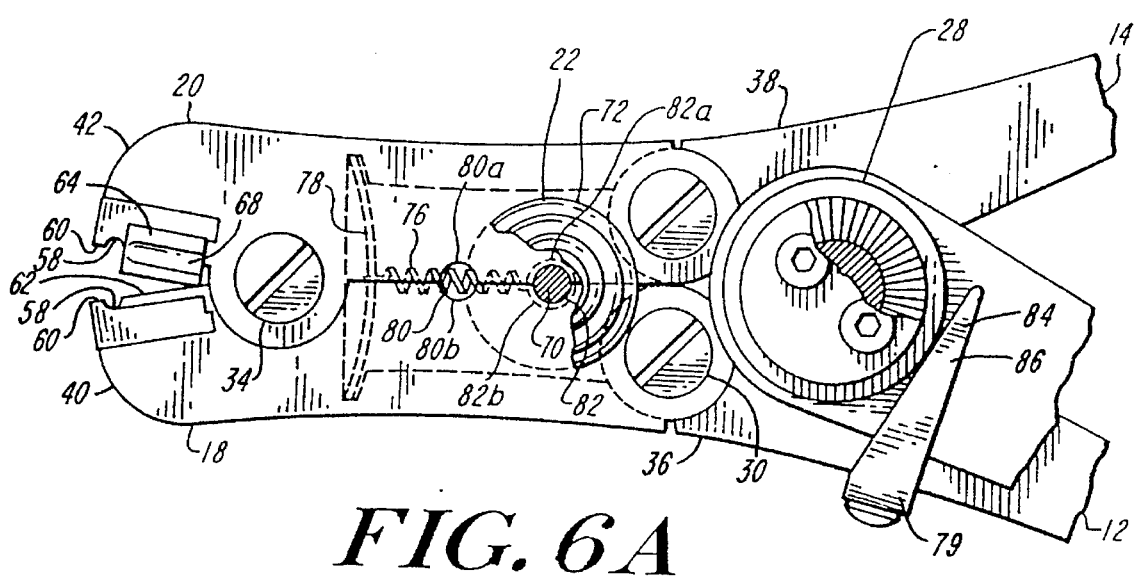
FIGS. 6(a), 6(b) and 6(c) are partial side elevation views of the jaws of the apparatus of FIG. 1 illustrating another aspect of the method of this invention.
Figure 6B:
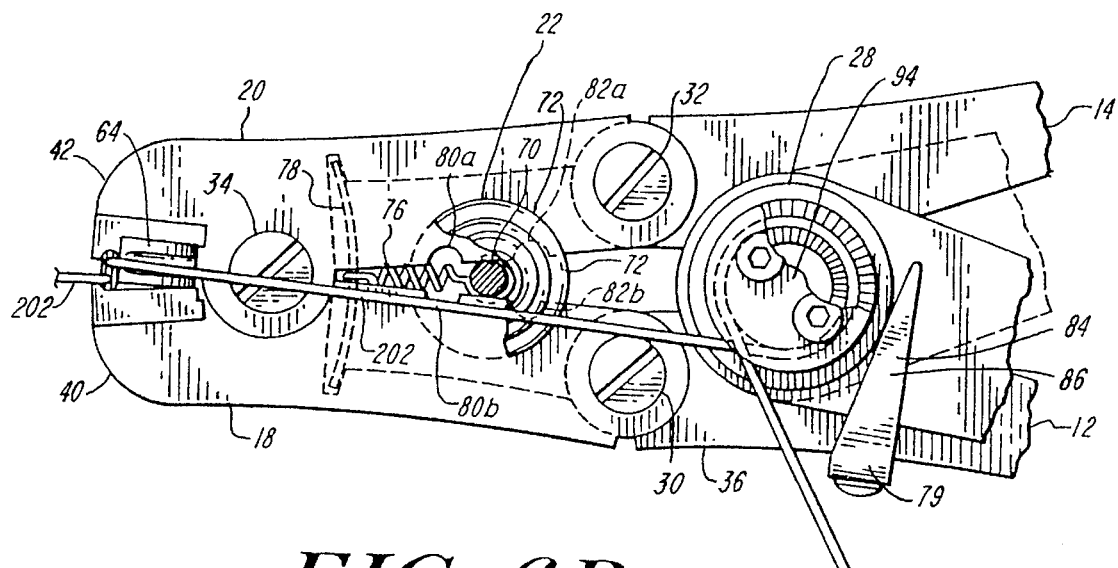
Figure 6C:
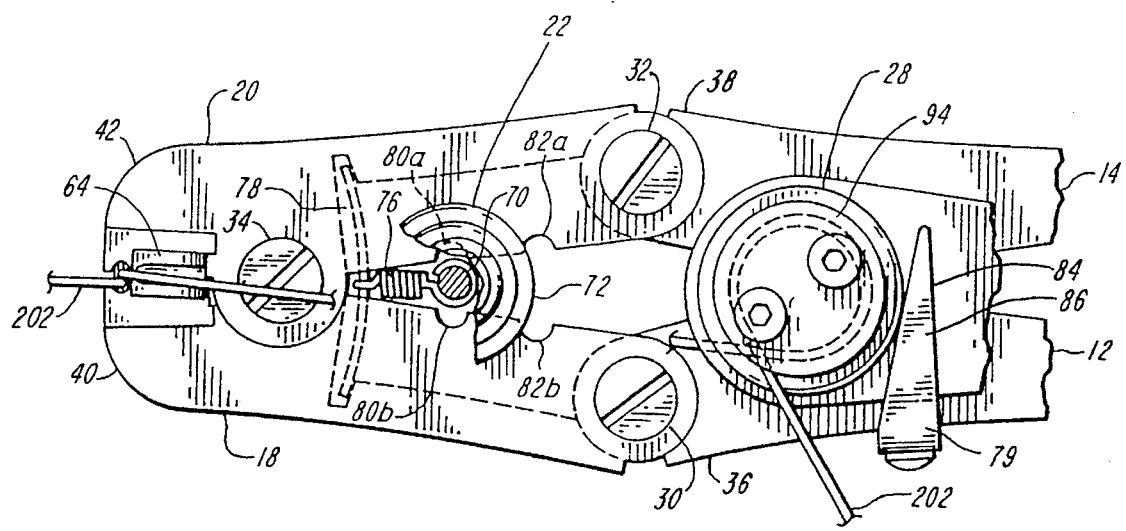

Positioned between pivots 30 and 32 and pivot 34 is a slidable stop 22. (See FIGS. 6(a)–6(c)). In one embodiment, stop 22 includes a spring 76 and a shaft 70 which passes laterally through apparatus 10 between jaws 18 and 20. Knobs 72 and 74 typically are mounted on opposite ends of shaft 70 and each knob 72 and 74 has concentric grooves or the like on an exterior surface to allow for gripping thereof. Shaft 70, and thus knobs 72 and 74 are permitted to slide toward and away from ends 40 and 42 between jaws 18 and 20. Spring 76 is a compression spring and is secured at one end to shaft 70 and at the other end to a fixed member 78 which extends between jaws 18 and 20. Spring 76 biases shaft 70 toward ends 40 and 42.

Semi-circular slots 80a, 80b and 82a, 82b are provided in respective jaws 20 and 18 and extend parallel to shaft 70. Confronting slots 80a and 80b in respective jaws 20 and 18 form one large circular slot 80, and confronting slots 82a and 82b form large circular slot 82. Shaft 70 nests in slots 80 and 82 to allow jaws 18 and 20 to be in contacting relation. Shaft 70 normally nests in slot 80 under the influence of spring 76. In this position, jaws 18 and 20 can be closed and reopened without interference from shaft 70.

If it is desired to use jaws 18 and 20 to hold or crimp a crimp member, handles 12 and 14 are-pivoted toward one another at proximal ends 13 and 15 to form a space between jaws 18 and 20. Shaft 70 is slid manually from slot 80 into slot 82 using knobs 74, and handles 12 and 14 are allowed to return to their normally spaced condition under the influence of spring 24. Handles 12 and 14 are again pivoted toward one another at respective proximal ends 13 and 15, causing ends 40 and 42 to move toward one another. The space between jaws 18 and 20 then becomes larger, permitting shaft 70 to ride out of slot 82 under the influence of spring 76 and into the space formed between jaws 18 and 20. Upon release of the pivoting force applied to handles 12 and 14, spring 24 urges handles 12 and 14 apart, capturing shaft 70 in the space between jaws 18 and 20 to retain ends 40 and 42 in a partially closed position. The spacing between ends 40 and 42 is determined by the position of shaft 70 relative to slots 80 and 82 in the space between jaws 18 and 20. The closer shaft 70 is to slot 80, the closer is the spacing between ends 40 and 42. The more handles 12 and 14 are squeezed together, the closer is the spacing between ends 40 and 42 and the farther shaft 70 travels toward slot 80. As a result, a crimp member 200 may be held in place within recesses 58 without crimping and with the desired applied force by selecting the proper spacing between ends 40 and 42. If handles 12 and 14 are squeezed farther together to push ends 40 and 42 farther together, the crimp member 200 disposed within recess 58 is crimped. At the same time, the space between jaws 18 and 20 is increased, thus releasing shaft 70 to return to slot 80 under the influence of spring 76. Thereafter, once crimp member 200 has been fully crimped, handles 12 and 14 are returned to their fully open position by spring 24 to allow removal of the crimped member.

Pivot 28 will now be described with particular reference to FIGS. 1, 2, 6(a), 6(b), 6(c) and 7. Pivot 28 includes a pair of ratchet mechanisms 90 and 92, capstans 94 and 95, and a coupling 96 (FIG. 7) between handles 12 and 14. Coupling 96 joins handles 12 and 14 and includes a ring 98 on handle 12 which is disposed between and is coaxial with two spaced, coaxial rings 97 and 99 on handle 14. Rings 97, 98 and 99 typically are machined from the material of their respective handles.

As shown in FIGS. 1 and 2, ratchet mechanisms 90 and 92 are disposed on opposite sides of pivot 28. However, mechanisms 90 and 92 are linked so that they rotate in synchronization. Mounted onto each mechanism 90 and 92 is an associated capstan 94 and 95 which grabs and coils an end of a surgical wire 202 in response to movement of handle 16.

Mechanism 90 includes a pair of coaxially stacked, opposed a discs 100 and 104 which are biased together by a spring 106. The opposed, mating surfaces of a discs 100 and 104 are formed of steps, each of which comprises a sloping, camming surface 108 and a shoulder 110 which is substantially perpendicular to surface 108. As in any conventional ratcheting mechanism, as one disc is rotated in one direction with respect to the other about their common central axis, surfaces 108 of one disc ride along the surfaces 108 of the other disc causing the discs to separate against the bias provided by spring 106. Discs 100 and 104 snap together again once shoulders 110 of one disc pass shoulders 110 of the other disc. However, if rotation is attempted in the other direction, shoulders 110 of one disc engage shoulders 110 of the other disc, precluding rotation of disc 104 with respect to disc 100 in that other direction.

Disc 100 is formed on a surface of mount 102. Mount 102 includes a shaft 103 which extends through rings 97, 98 and 99, as well as through a hole in the center of disc 104, the center of spring 106 and a hole in the end of handle 16. The hole in the center of disc 104 preferably is hexagonal in shape. A hex nut 112 is attached to the end of handle 16 and surrounds the hole therein. Nut 112 seats in the hole in the center of disc 104 so that disc 104 rotates in response to the rotation of handle 16.

Mechanism 92 includes a similar set of components, including a disc 120, a disc 122 and a spring 124. Discs 120 and 122 are coaxially stacked and are urged into contact by spring 124. Confronting surfaces of discs 120 and 122 carry steps comprising sloping camming surfaces 126 and shoulders 128, similar to surfaces 108 and shoulders 110 found on the surfaces of discs 100 and 104. A shaft 130 is affixed to the center of disc 120 and passes through a hole in the center of disc 122 and a hole in the center of spring 124. Projections 132 on the end of shaft 130 mate with corresponding grooves formed on the end of shaft 103, while projections 133 on the end of shaft 103 extend into corresponding grooves formed on the end of shaft 130. This connection locks shaft 130 to shaft 103. Rotation of disc 100 by handle 16 produces comparable rotation of disc 120.

Figure 7:
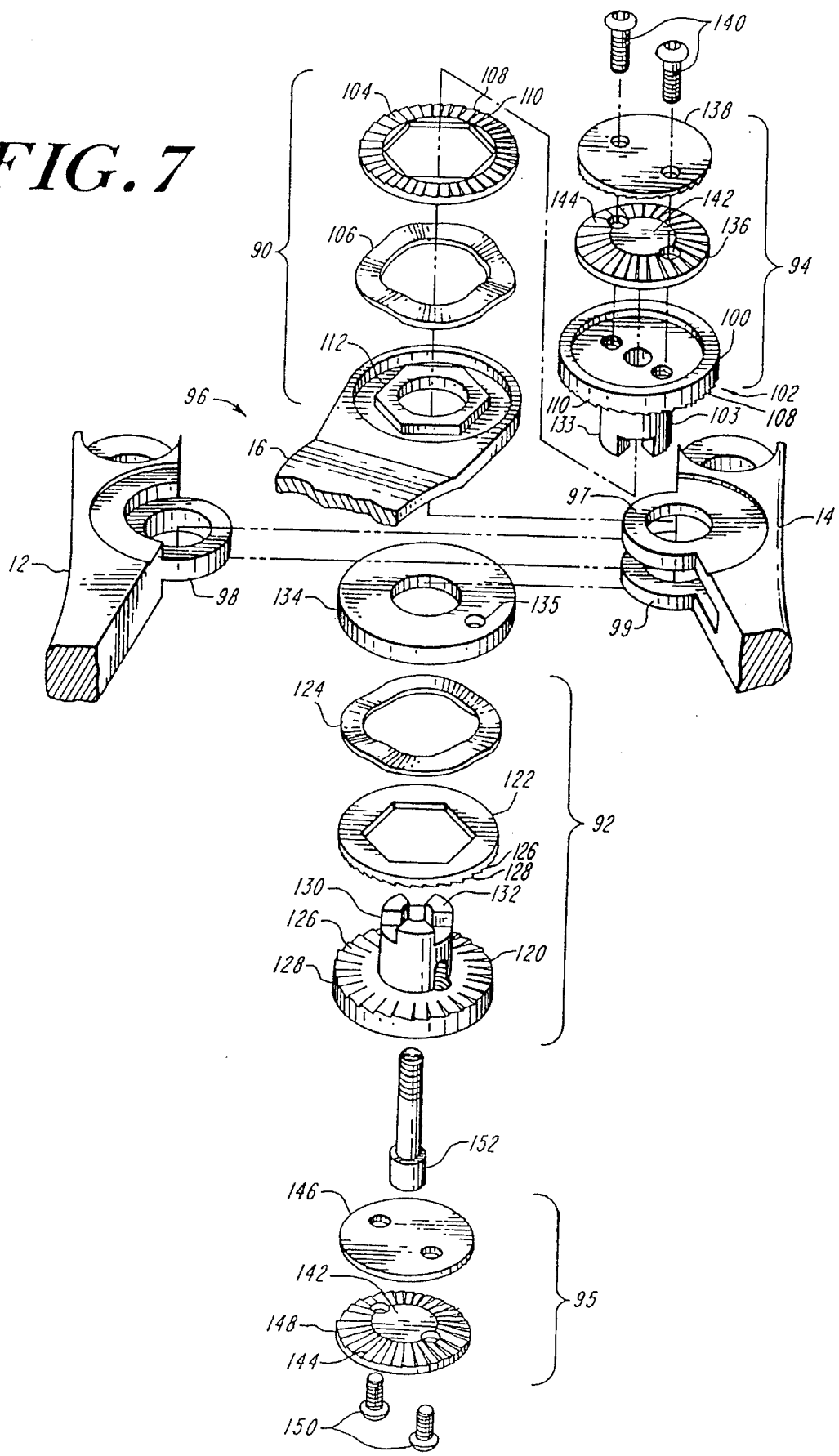
FIG. 7 is a perspective, exploded view of the pivot of the apparatus of FIG. 1.

Circular disc 134 is secured against rotation with respect to handle 14 by means of a screw (not shown) extending through hole 135. A hex nut (not shown) secured to a side of disc 134 opposite handle 14 seats in a hexagonal hole in disc 122. Thus, disc 122 is locked against rotation with respect to handle 14. Therefore, rotation of disc 120 is permitted only in a direction in which surfaces 126 of disc 120 are permitted to slide along similarly formed surfaces 126 on disc 122, a counter-clockwise direction as shown in FIG. 7. However, should an attempt to be made to rotate disc 120 in the opposite direction, such as a clockwise direction as shown in FIG. 7, such rotation would be prevented by the engagement of shoulders 128 on disc 120 with shoulders 128 on disc 122. Therefore, disc 120 can be rotated in only the one direction. Since disc 120 is locked to disc 100 by shafts 130 and 103, disc 100 is also prevented from rotating in an opposite direction, or in a clockwise direction as shown in FIG. 7. As a consequence, handle 16 is only permitted to rotate discs 100 and 120 in a single direction, a counter-clockwise direction as shown in a FIG. 7. Handle 16 is permitted to return to its home position under the influence of spring 26. Rotation of disc 104 with respect to disc 100 in that opposite direction, a clockwise direction as shown in FIG. 7, is permitted, since surfaces 108 on disc 100 ride along surfaces 108 on disc 104, urging discs 100 and 104 apart under the influence of spring 106 as handle 16 rotates. When handle 16 is rotated in a counter-clockwise direction as shown in FIG. 7, shoulders 110 on disc 100 engage shoulders 110 on disc 104 causing discs 102 and 104 to rotate in unison in a counter-clockwise direction. This rotation also produces rotation of disc 120 in the same direction or a counter-clockwise direction as shown in FIG. 7. In this manner, both ratchet mechanisms 90 and 92 are operated in synchronism.

Capstans 94 and 95 will now be described with particular reference to FIG. 7. Capstans 94 and 95 each may comprise any mechanism for applying a tractive force to a wire, but preferably are formed as shown in FIG. 7 and are preferably adapted to have a wire coiled thereabout as they are rotated. Capstan 94 is associated with ratchet mechanism 90, while capstan 95 is associated with ratchet mechanism 92. As can be seen, capstans 94 and 95 are disposed on opposite sides of handles 12 and 14. Capstan 94 includes a pair of spaced plates 136 and 138. Plates 136 and 138 are held together by screws 140 or other like fastening devices. Plate 136 seats in a recess in mount 102, and screws 140 are inserted into correspondingly threaded holes in mount 102. Each plate 136 and 138 has a generally flat center portion 142 which abuts a similarly configured center portion 142 in the other of plates 136 and 138. Each plate 136 and 138 has an annularly shaped, toughened surface 144 which slopes downwardly away from portion 142 to the perimeter of the plate. Typically, although not necessarily, surface 144 comprises a series of radially extending steps. The steps include surfaces angled with respect to the bottom surface of plates 136 and 138 and shoulders which are generally perpendicular to the angled surfaces. Capstan 94 is adapted to grip and coil a portion of the wire 202 in response to ratcheting movement of handle 16. Thus, surfaces 144 should be configured to facilitate the gripping and coiling of the wire. As the wire is tightened on capstan 94, because of the slope of surface 144, the wire will migrate toward the center or toward portion 142, thus allowing accommodation for additional wire to be wound about the capstan.

Capstan 95 is substantially identical to capstan 94 and includes plates 146 and 148. Plates 146 and 148 are held in place by screws 150 or other like fixation devices. Screws 150 are threadably mounted onto disc 120. Both of plates 146 and 148 include a sloping, roughened surface 144 and central portion 142 like plates 136 and 138, and are otherwise substantially identical to plates 136 and 138 of capstan 94.

Pivot 28 is held together by a screw 152, the head of which seats in disc 120, and the shaft of which passes through disc 120 and rings 97, 98 and 99. The shaft of screw 152 is threadably secured to mount 102.

Wire holder 84 is typically U-shaped or is formed into the shape of a rectangle in which one side is missing, and includes two arms 86 and 87 and a cross member 79 linking arms 86 and 87. Member 79 is secured to handle 12 by a screw or the like and serves to anchor holder 84. Arms 86 and 87 each extend beneath an associated capstan 94 or 95. Each arm 86 and 87 is provided with a shoulder 91 and a finger 89 which extends beyond shoulder 91. The end of a wire wrapped about capstan 94 or 95 is bent around shoulder 91 to hold it in place during the beginning stages of the wire tightening procedure. Finger 89 prevents the wire from sliding off shoulder 91. The wire is restrained in the other direction by either handle 16 or the surfaces of handles 12 and 14. Holder 84 also includes a shoulder 77 which acts as a stop to limit the movement of handle 16 in a clockwise direction,.as shown in FIG. 1, under the influence of spring 26. Shoulder 77 defines the home position of handle 16.

Figure 3:
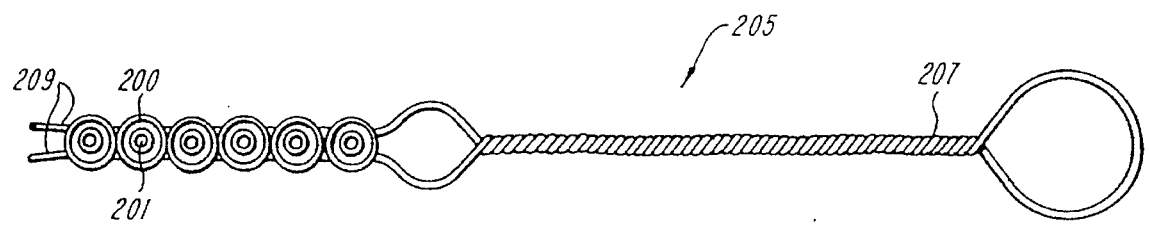
FIG. 3 is a top plan view showing the crimp members and dispenser of this invention.

Crimp member 200 and a dispenser 205 will now be described with reference to FIG. 3. Each crimp member 200 typically is donut-shaped and includes a ring with a central, axially aligned hole 201 and two generally parallel channels 203 (FIG. 5) extending in a direction generally normal to the central axis of the ring of member 200. Channels 203 extend through the ring on either side of hole 201 and may or may not intersect hole 201. Typically, crimp member dispenser 205 includes a handle 207 and two parallel arms 209 which are bent slightly outwardly away from one another at their distal tips. Arms 209 extend through the two channels 203 of members 200 and allow members 200 to be mounted sequentially on arms 209. Arms 209 are spaced apart a distance adjacent handle 207 which is greater than their spacing in the middle of arms 209 to limit movement of members 200 toward handle 207. In one embodiment, dispenser 205 is formed of a single wire bent in half and twisted adjacent the bend to form handle 207.

The operation of apparatus 10, along with the method of this invention will now described with particular reference to FIGS. 4–6(c). It is to be understood that this invention may be used for any operation in which it is desired to use a surgical wire, such as, for example, reconstructive spine surgery, spine trauma surgery, total hip arthroplasty, open-heart surgery, closures of the sternum, oral/facial surgery to fix mandibular fractures, repair of trochanteric osteotomies, the repair, reconstruction or augmentation of ruptured or sprained ligaments and tendons, and fracture fixation, including fixing of long bone fractures, repair of olecron fractures, and repair of patella fractures. It is also to be understood that wire 202 may be a single strand of wire, or a cable formed of multiple strands of wire twisted together. Wire 202 may be formed of metal, although this invention also may be used with a non-metallic wire formed of a plastic material such as NYLON®, DELRIN®, DACRON®, or KEVLAR® or any other biologically compatible material. Such a non-metallic wire may either be a monofilament wire or a multi-filament cable formed of strands twisted or braided together. Such a non-metallic wire is preferred in some applications, since it does not degrade or obscure CAT scans or MRI images. Also, such non-metallic wires tend to have higher fatigue strengths. For simplification, no bone parts or pieces are shown in the drawings, but it is to be understood that wire 202 would encircle a bone or bone fragments, or soft tissues.

Figure 4A:
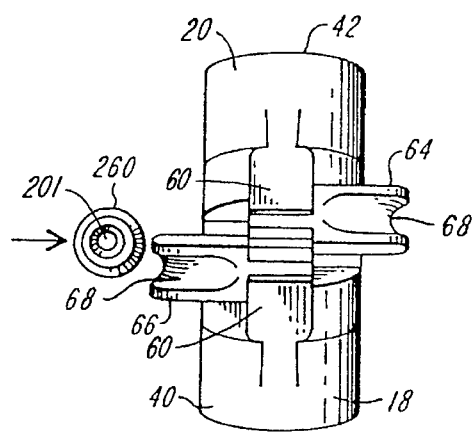
FIGS. 4(a), 4(b), 4(c) and 4(d) are plan views of the jaws of the apparatus of FIG. 1 illustrating one aspect of the method of this invention.
Figure 4B:
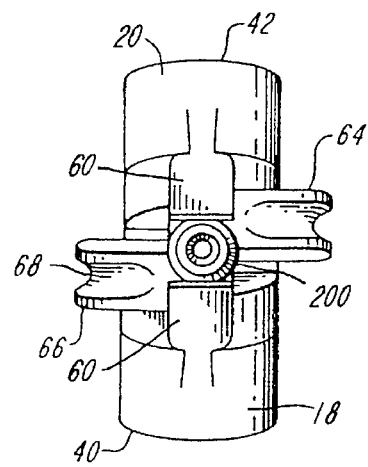
Figure 4C:
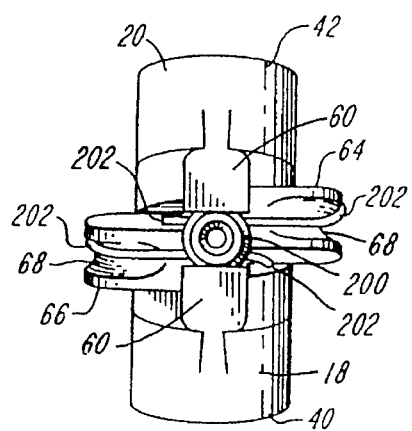

To commence the process, shaft 70 is moved by manipulation of knobs 72 and 74 into slot 82 in the manner previously discussed. A crimp member 200 is lowered into recesses 58 in nose ends 40 and 42. This procedure is accomplished, as shown in FIGS. 4(a)–(c). When it is desired to insert a crimp member 200 into recesses 58, dispenser 205 is positioned such that the crimp member 200 which is disposed on the distal ends of arms 209 is positioned within recesses 58 while ends 40 and 42 are in a fully opened position. Handle 207 of dispenser 205 is held by the surgeon in one hand, while apparatus 10 is held in his other hand. While the most distally disposed crimp member 200 is being held within recesses 58, the surgeon begins pivoting the proximal ends of handles 12 and 14 toward one another to close jaws 18 and 20 to grasp crimp member 200. Once crimp member 200 is held in place without deformation by jaws 18 and 20, dispenser 205 is removed by withdrawing the proximal ends of arms 209 from channels 203 of crimp member 200.

As the proximal ends of handles 12 and 14 are pivoted toward one another to grasp crimp member 200, shaft 70 pops out of slot 82 under the influence of spring 76, as a gap is formed between jaws 18 and 20. Once the desired force is applied to crimp member 200 by jaws 18 and 20, the proximal ends of handles 12 and 14 are no longer pivoted toward one another. At this point, shaft 70 is disposed intermediate slots 80 and 82 and is trapped in that position by jaws 18 and 20. Shaft 70 prevents spring 24 from returning handles 12 and 14 to their fully separated positions and thus prevents ends 40 and 42 from separating. Thus crimp member 200 is tightly held in recesses 58 without being crimped.

Thereafter, the surgical wire 202 is wrapped about the bone or bone fragments in accordance with the desired surgical procedure. One end of wire 202 is inserted through channel 203 of crimp member 200 from the side of ends 40 and 42 on which guide 64 is located. Wire 202 is passed through the channel 203 which is not associated with guide 64, and wire 202 exits the other side of channel 203 directly above guide 66. This free end of wire 202 passes through a slot 68 in guide 66 and is wrapped about capstan 95 between plates 146 and 148 in a clockwise direction, as shown in FIG. 2. This end of wire 202 is wrapped around capstan 95 once and is bent about shoulder 91 of arm 87 and away from finger 89. Similarly, the other end of wire 202 is passed through the other channel 203 of member 200 from a side of the apparatus having guide 66. This end of wire 202 exits channel 203 directly aligned with guide 64 and passes through slot 68 thereof. Wire 202 then is wrapped about capstan 94 between plates 136 and 138 in a counter-clockwise direction, as shown in FIG. 1. After being wrapped once about capstan 94, the end of the wire is bent about shoulder 91 of arm 86 and away from finger 89.

Figure 5:
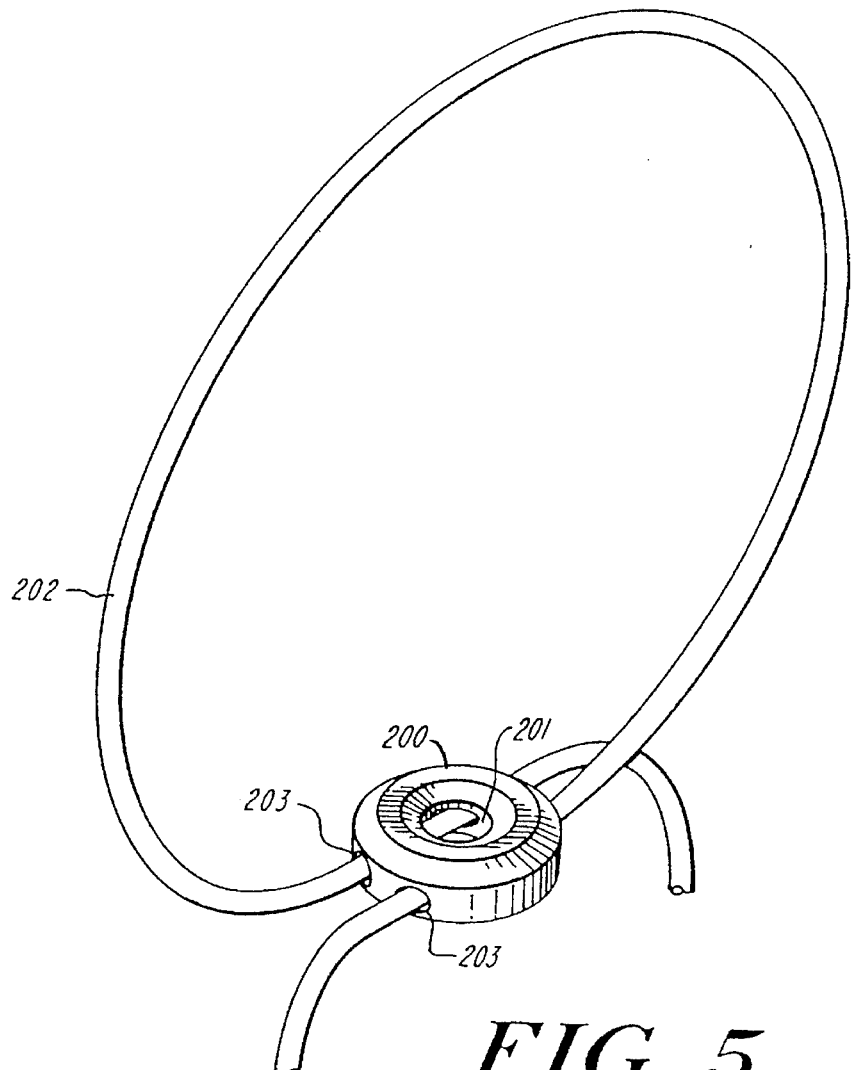
FIG. 5 is a perspective view illustrating the use of the surgical wire in conjunction with the crimp member of this invention.

At this point, surgical wire 202 is substantially in the configuration shown in FIG. 5. To tighten the wire, ratchet handle 16 is moved repeatedly in a counter-clockwise direction as shown in FIG. 1 and in FIG. 6(a). This operation can be performed with one hand. Handle 14 resides in the palm, and the surgeon's fingers are wrapped about ratchet handle 16 to repeatedly draw handle 16 toward handle 14 and release handle 16 to allow handle 16 to return to its home position, as shown in FIG. 1. This repeated motion of ratchet handle 16 wraps both ends of wire 202 simultaneously around capstans 94 and 95. As more wire is wrapped around each capstan, wire 202 tends to move inwardly along surfaces 144 toward center portion 142. While the wire was initially wrapped about arms 86 and 87 to hold it in place, the free ends are released once the tightening process begins. Once the desired tractive force on wire 202 has been achieved, the tightening process has been completed.

Thereafter, wire 202 is crimped in position. This crimping is accomplished by pivoting the proximal ends of handles 12 and 14 farther together. Typically, this crimping process can be accomplished using a single hand, since the mechanical advantage gained by these handles with respect to the ends of the jaws is substantial. The length of handles 12 and 14 is much greater than the very short distance from pivot 28 to pivots 30 and 32. Likewise, the distance from pivots 30 and 32 to pivot 34 is much greater than the distance from pivot 34 to ends 40 and 42. Therefore, an ordinary physician using one hand can apply the pressure necessary to adequately crimp crimp member 200.

As the proximal ends of handles 12 and 14 are squeezed together, ends 40 and 42 close and crimp member 200 deforms. At the same time, the spacing between jaws 18 and 20 increases and shaft 70 begins to move toward pivot 34 under the influence of spring 76, until shaft 70 again resides in slot 80. Once shaft 70 has returned to slot 80, jaws 18 and 20 are permitted to completely open under the influence of spring 24 to allow removal of the crimped crimping member 200.

Figure 4D:
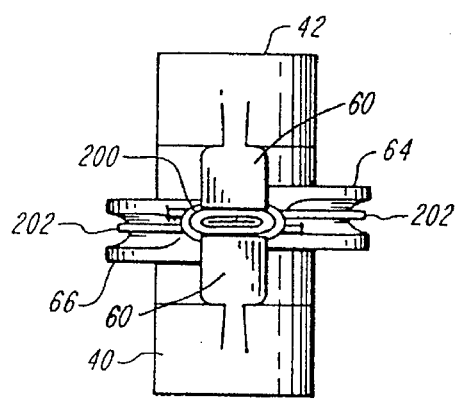

Member 200 is deformed into a very small package, as shown in FIG. 4(d), and holds wire 202 in the desired location with the desired tractive force. The provision of the central hole 201 allows the desired deformation of crimping member 200. The resulting size of member 200 is not substantially larger than the combined width of the two sections of wire 202. For this reason, the resulting crimped wire produces little irritation and can be used in percutaneous locations.

At this point, the process is complete, and the ends of wire 202 can be cut closely adjacent the crimped member 200. The remaining ends of wire 202 can be removed from capstans 94 and 95 and discarded.

Figure 8:
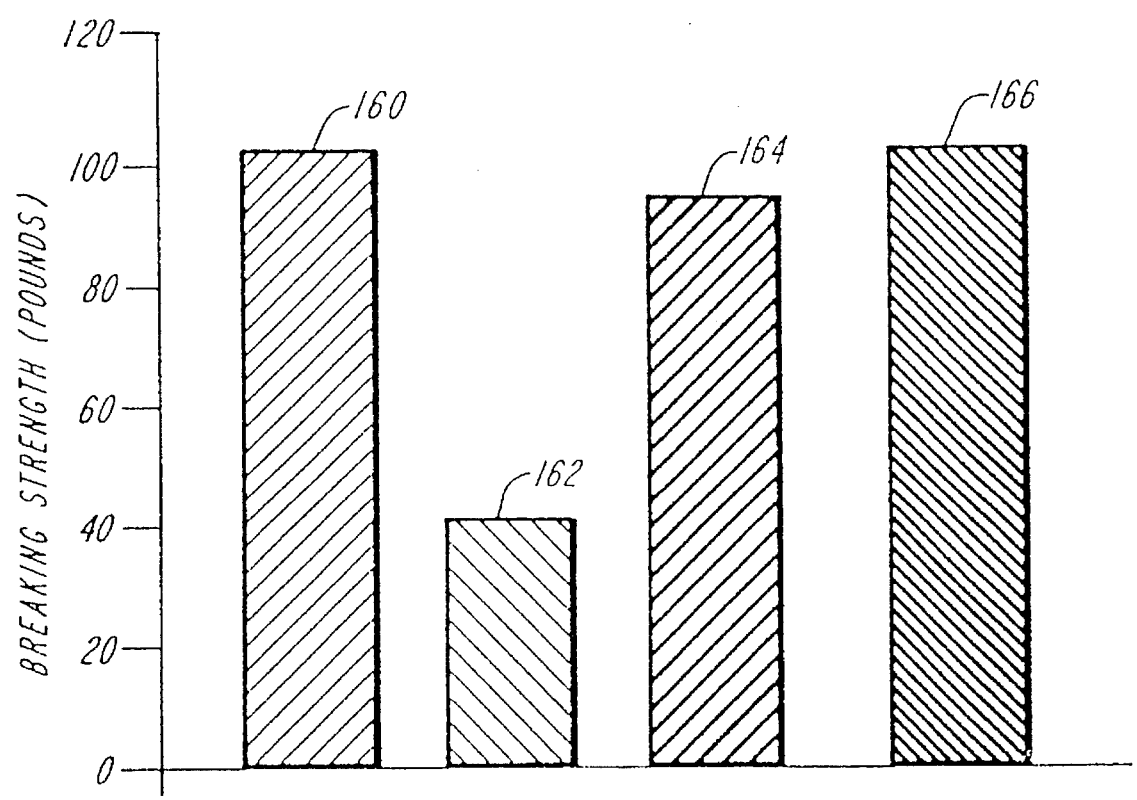
FIG. 8 is a bar graph showing the tensile strength of wire fastened using different methods.

FIG. 8 illustrates the tensile strength of solid 18 gauge surgical wire compared with wire fastened using various methods. FIG. 8 is a bar graph in which the vertical axis represents strength in pounds. Bar 160 represents the tensile strength of solid 18 gauge 316 stainless steel wire. Bar 162 represents the tensile strength of 18 gauge stainless steel wire which has been twisted together. Bar 164 represents the tensile strength of 18 gauge stainless steel wire which has been tied in a square knot. Bar 166 represents the tensile strength of 18 gauge stainless steel wire which has been crimped according to the method of the present invention. As can be seen, wire which has been crimped according to the method of this invention has substantially the same tensile strength as solid, uncrimped 18 gauge stainless steel wire.

As can be seen from the foregoing description, using the method and apparatus of this invention, a single physician can perform the entire operation with little or no assistance from another physician or an assistant. Apparatus 10 is sufficiently small and is so configured that it can be grasped and operated by one hand. Each step of the process requires no more than two hands. Furthermore, only a single tool performs both the tightening and crimping processes. No additional elements or pieces of apparatus are required to either tighten or crimp. Moreover, the resulting crimped wire has the same strength as uncrimped wire and the size of the crimp is so small, it can be placed percutaneously.

In view of the above description, it is likely that modifications and improvements will occur to those skilled in the art which are within the scope of this invention. The above description is intended to be exemplary only, the scope of the invention being defined by the following claims and their equivalents.

What is claimed is:

1. Apparatus for tightening a surgical wire and for crimping together two different portions of the wire with a desired tractive force, said apparatus comprising:

a pair of pivotally connected operating handles, each of said handles having a distal end and a proximal end;

a pair of opposed jaws operatively connected to said distal ends of said operating handles, said jaws being opened and closed in response to movement of said operating handles, said jaws defining a recess therebetween for holding a crimp member;

a pair of mechanisms disposed intermediate said jaws and said proximal ends of said operating handles for applying the tractive force to the wire, said mechanisms each being adapted to receive one of the two portions of the wire;

a pivotally mounted ratchet handle coupled to both of said mechanisms for simultaneously activating both of said mechanisms; and apparatus for retaining said jaws in a partially closed position for holding a crimp member tightly in a non-deformed condition, said retaining apparatus comprising a spring for biasing said jaws into an open position, and a stop for preventing said jaws from opening under the influence of said spring, the position of said stop being adjustable to allow positioning of said laws with a desired spacing, a slot disposed in said jaws adapted to receive said stop, said jaws being fully openable when said stop resides in said slot, and a second spring for urging said stop into said slot when said jaws are closed sufficiently to deform the crimp member.

2. Apparatus as recited in claim 1 further comprising a second slot disposed between said jaws, said jaws being fully openable when said stop resides in said second slot, said stop returning toward said first slot under the influence of said second spring as said jaws are closed toward one another.

3. Apparatus as recited in claim 1 further comprising guides for guiding portions of the wire from said jaws toward associated mechanisms.

4. Apparatus as recited in claim 1 wherein said ratchet handle includes a proximal end disposed between said operating handles substantially in the plane of said operating handles.

5. Apparatus for tightening a surgical wire and for crimping together different portions of the wire with a desired tractive force, the wire having two different portions, said apparatus comprising:

a pair of pivotally connected operating handles, each handle having a distal end and a proximal end;

a pair of opposed jaws operatively connected to said distal ends of said operating handles, said jaws being opened and closed in response to movement of said operating handles, said jaws defining a recess therebetween for holding a crimp member;

a pair of mechanisms disposed intermediate said jaws and said proximal ends of said operating handles for applying the tractive force to the wire, said mechanisms each being adapted to receive one of the two portions of the wire;

a pivotally mounted ratchet handle coupled to both of said mechanisms for simultaneously activating both of said mechanisms; and a spring disposed on said ratchet handle biasing said ratchet handle into a home position, said spring including a preformed strip of metal having two ends, one end of said strip of metal being attached to a proximal end of said ratchet handle, the other end of said strip of metal being secured to a cam follower which rides along an interior surface of one of said operating handles.

6. A method for the tightening and crimping of a surgical wire, said method comprising the steps of:

wrapping a length of wire around at least a portion of a body part so that two portions of the wire are disposed on the same side of the body part;

placing a crimp member having first and second parallel channels in pivotally mounted jaws of a crimping apparatus so that said channels extend parallel to a pivot axis defined by said pivotally mounted jaws;

passing each of said two portions of the wire through an associated one of said first and second channels in the crimp member;

passing each of said two portions of the wire along an associated guide member to change the direction of the wire portions from parallel to the pivot axis to substantially perpendicular to the pivot axis;

wrapping one of said two portions of the wire about an associated first tightening mechanism;

wrapping the other of the said two portions of the wire about a second tightening mechanism;

tightening the wire about the body part by actuating the first tightening mechanism to pull said one portion of the wire in a direction parallel to the pivot axis and generally parallel to the other of said two portions of the wire;

actuating the second tightening mechanism simultaneously with actuation of the first tightening mechanism to apply a tractive force to the other portion of the wire during said tightening step to pull said other portion of the wire in a direction parallel to the pivot axis and opposite to the direction in which said one portion is pulled; and crimping the two portions of the wire together by deforming the crimp member with the jaws of the crimping apparatus.

* * * * *